(12) United States Patent
Liu et al.

(10) Patent No.: US 8,246,248 B2
(45) Date of Patent: Aug. 21, 2012

(54) STROKE CONTROL DEVICE

(75) Inventors: Junhua Liu, Shenzhen (CN); Shanzhi Huang, Shenzhen (CN)

(73) Assignee: Shenzhen Mindray Bio-Medical Electronics Co., Ltd., Shenzhen (CN)

( * ) Notice: Subject to any disclaimer, the term of this patent is extended or adjusted under 35 U.S.C. 154(b) by 609 days.

(21) Appl. No.: 12/543,106

(22) Filed: Aug. 18, 2009

(65) Prior Publication Data

US 2010/0071489 A1  Mar. 25, 2010

(30) Foreign Application Priority Data

Sep. 24, 2008  (CN) .......................... 2008 1 0216532

(51) Int. Cl.
 *H05G 1/02* (2006.01)
(52) U.S. Cl. ....................................... 378/197
(58) Field of Classification Search .................. 378/196, 378/197, 177, 181, 91, 190; 74/89.22
 See application file for complete search history.

(56) References Cited

U.S. PATENT DOCUMENTS

| | | | |
|---|---|---|---|
| 3,496,354 A * | 2/1970 | Forsyth ............................ | 378/41 |
| 4,412,346 A * | 10/1983 | Takenouti et al. ............. | 378/181 |
| 4,501,011 A | 2/1985 | Hauck et al. | |
| 5,023,899 A * | 6/1991 | Ohlson .......................... | 378/196 |
| 5,048,070 A | 9/1991 | Maehama et al. | |
| 5,734,694 A * | 3/1998 | Khutoryansky et al. ...... | 378/197 |
| 6,926,442 B2 * | 8/2005 | Stockl ............................ | 378/197 |
| 7,182,511 B2 * | 2/2007 | Boomgaarden et al. ...... | 378/197 |
| 2006/0071138 A1 | 4/2006 | Steger et al. | |

FOREIGN PATENT DOCUMENTS

| | | |
|---|---|---|
| CN | 2431702 Y | 5/2001 |
| CN | 1424866 A | 6/2003 |
| CN | 1552286 A | 12/2004 |
| JP | 2008531231 A | 8/2008 |

* cited by examiner

*Primary Examiner* — Irakli Kiknadze
(74) *Attorney, Agent, or Firm* — Kory D. Christensen; Stoel Rives LLP

(57) ABSTRACT

A stroke control device includes a first driving mechanism driving a carrier into a linear movement, the first driving mechanism comprising a rotating shaft arranged rotatably on a main body for receiving power input, a stopper being configured to move linearly, first and second limit switches defining a linear movement stroke of the stopper, and a second driving mechanism for driving the stopper into a linear movement, wherein the second driving mechanism includes an input member rotating synchronously with the rotating shaft and an output member on which the stopper is fixed, wherein the linear movement stroke of the stopper is less than the linear movement stroke of the carrier, and wherein the first and second limit switches are provided on the main body with a spacing therebetween and are both arranged on a path of the linear movement of the stopper.

10 Claims, 3 Drawing Sheets

STROKE CONTROL DEVICE

RELATED APPLICATIONS

This application claims priority to Chinese Patent Application No. 200810216532.3, filed Sep. 24, 2008, which is hereby incorporated by reference in its entirety.

TECHNICAL FIELD

This disclosure relates to a stroke control device for implementing stroke control of a linear movement of a carrier.

DETAILED DESCRIPTION

Figure 1:
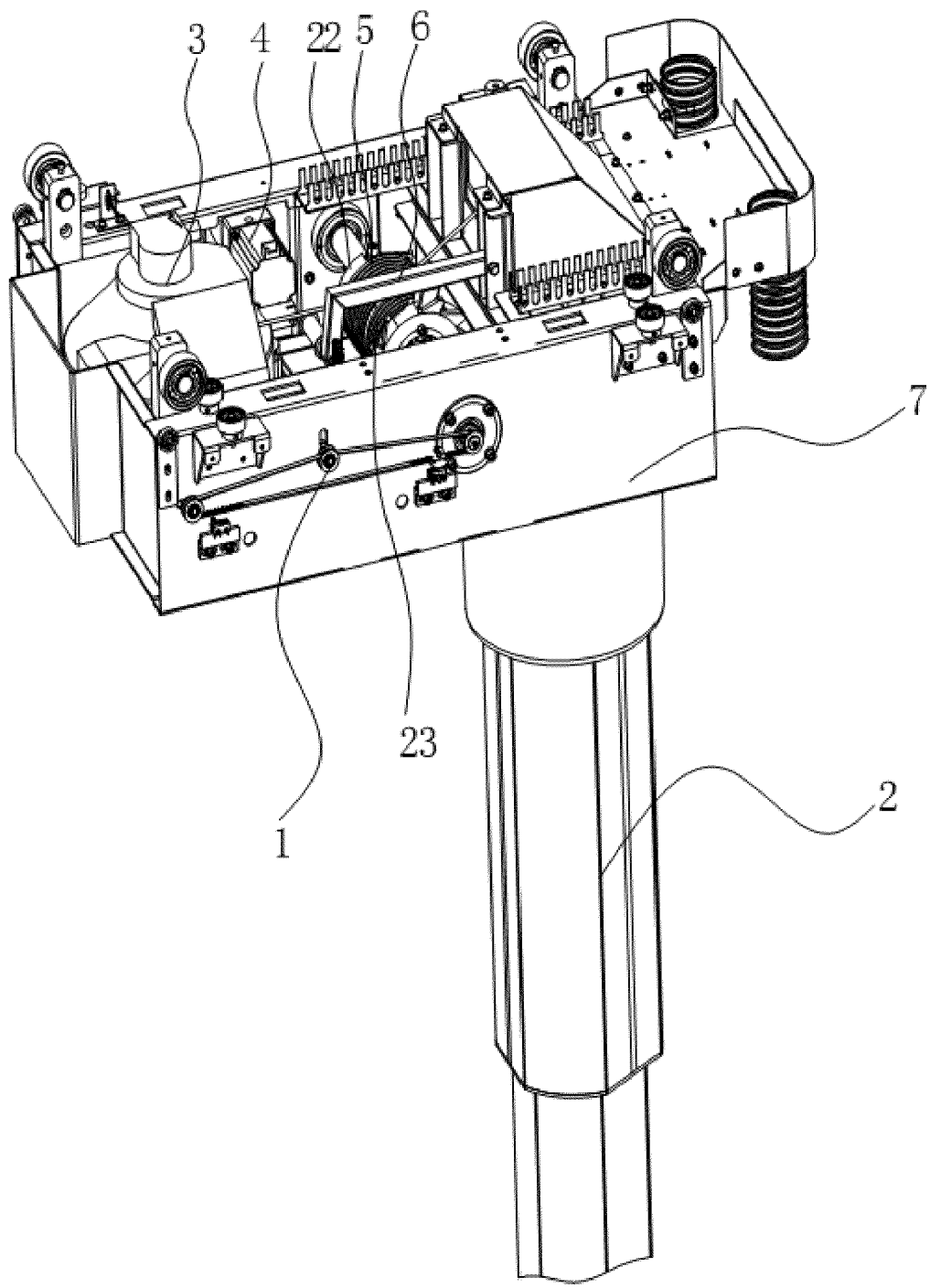
FIG. 1 is a perspective view of a stroke control device.

Stroke control of the up-and-down movement of an X-ray tube of a suspension type medical X-ray photograph system typically includes mechanical switches for controlling limit positions. The up-and-down movement of the X-ray tube may be realized through a drum having a drum shaft. The limit control of the X-ray tube may be accomplished in two ways.

First, gears may be mounted on the drum shaft, through which a worm and worm gear are driven, and a vertical up-and-down stroke of the X-ray tube is converted synchronously into a rotational stroke of the worm and worm gear, such that the vertical up-and-down stroke of the X-ray tube eventually completes the triggering of the limit switches when the worm gear is rotated by about 90°. For example, If the effective stroke of the X-ray tube is 1500 mm, a stroke of the worm gear of 90° will correspond to a stroke of the X-ray tube of 1500 mm. Thus, each rotation at a tiny angle of the stopper on the worm gear for triggering the limit switch corresponds to a large stroke of the X-ray tube, making it difficult to adjust the stroke of the X-ray tube via the stopper.

Second, a grating scale may be used for detecting positions. In such a configuration, a telescopic bar of the grating scale is driven by a sprocket and a chain to detect its stroke. Unfortunately, the grating scale occupies a large space and is not convenient for installation. Furthermore, such stroke control belongs to electrical control.

It is desirable to be able to adjust the stroke range conveniently and be able to ensure a desired movement stroke effectively. Accordingly, in one embodiment of the present disclosure, a stroke control device may include a first driving mechanism for driving a carrier into a linear movement, a stopper that is able to move linearly, first and second limit switches defining a linear movement stroke of the stopper, and a second driving mechanism for driving the stopper into a linear movement.

The first driving mechanism may include a rotating shaft arranged rotatably on a main body for receiving power input. The second driving mechanism may includes an input member rotating synchronously with the rotating shaft and an output member on which the stopper is fixed. The linear movement stroke of the stopper may be less than the linear movement stroke of the carrier. The first and second limit switches may be provided on the main body with a spacing therebetween and may be both arranged on a path of the linear movement of the stopper.

In one embodiment, the input member is a synchronous pulley, and the output member is a synchronous belt. The second driving mechanism may further include a driven pulley, where the synchronous belt is tensioned on the synchronous pulley and the driven pulley, the synchronous pulley is fixed on the rotating shaft, the driven pulley is arranged rotatably on the main body, and the stopper is fixed on the synchronous belt.

The driven pulley may be arranged rotatably on a supporting axle through a bearing, the supporting axle being arranged on the main body on which an adjusting slot is provided. An end portion of the supporting axle may extend into the adjusting slot.

In one particular configuration, the number of the driven pulleys is two, and these two driven pulleys and the synchronous pulley present a triangular distribution. In such a configuration, all of the rotating shaft and the supporting axles of the two driven pulleys may be disposed horizontally and parallel to each other. Both of the first and second limit switches may be respectively arranged on the main body via a fixture with an adjustable mounted position.

In one embodiment, the input member is a sprocket, the output member is a chain, and the second driving mechanism further includes a driven sprocket. The chain may be tensioned on the sprocket and the driven sprocket, with the sprocket being fixed on the rotating shaft, the driven sprocket being arranged rotatably on the main body, and the stopper is fixed on the chain.

The input member may be a gear, which is fixed on the rotating shaft. The output member may be a rack that meshes with the gear. The stopper may be fixed on the rack, and the rack may slidably fit in a linear guide rail fixed on the main body.

In one configuration, the first driving mechanism further includes a drum fixed on the rotating shaft and a tether wound on the drum. The carrier may be connected with the tether, and the diameter of the drum may be larger than the diameter of the input member. The tether may be further connected with a balancer for gravity balance of the carrier.

The carrier may be a telescopic cylinder, which is used in an X-ray photograph system and by which an X-ray tube is hung. The telescopic cylinder may be connected with the tether and may move up and down in a vertical direction.

Figure 2:
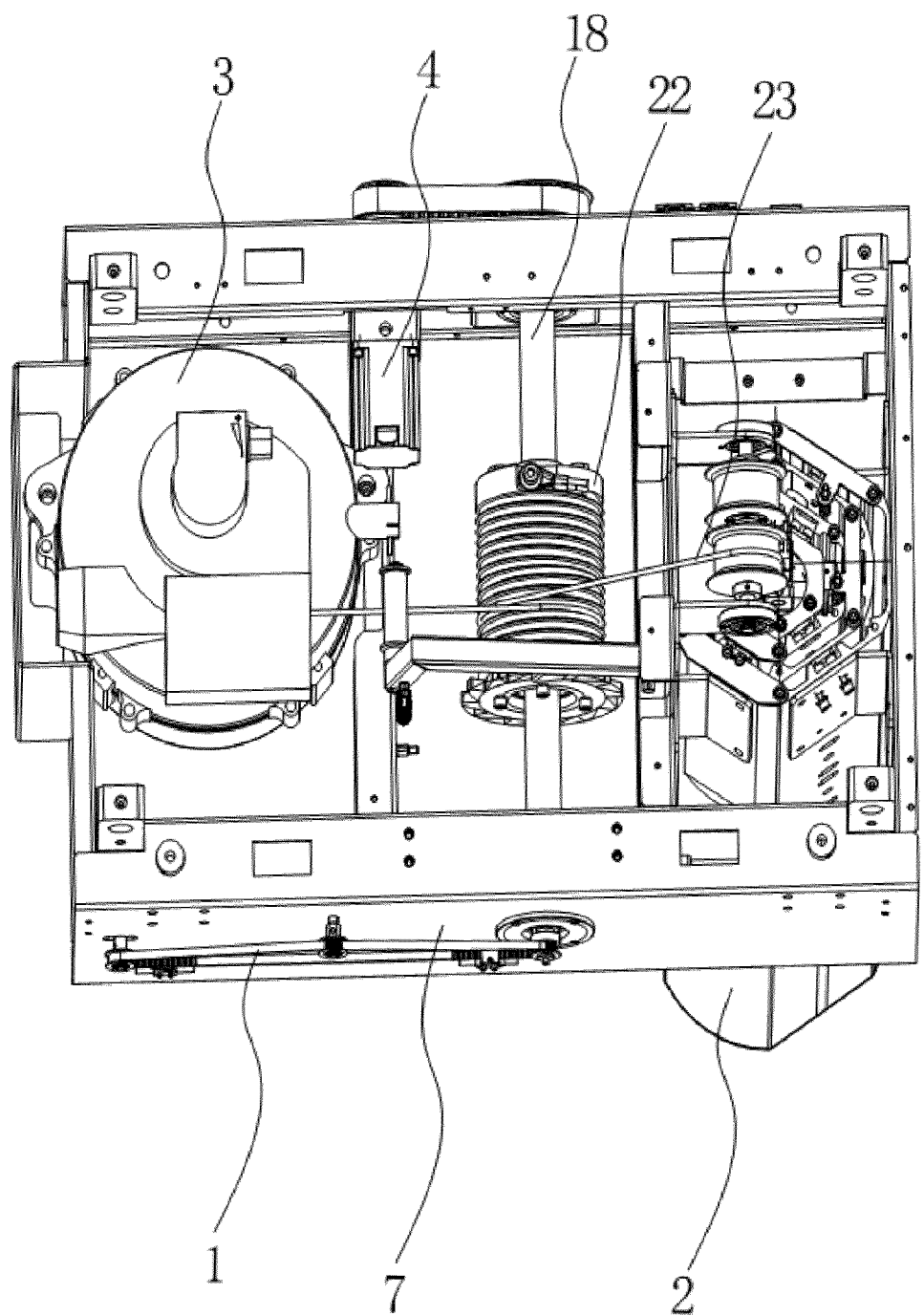
FIG. 2 is another perspective view of a stroke control device.
Figure 3:
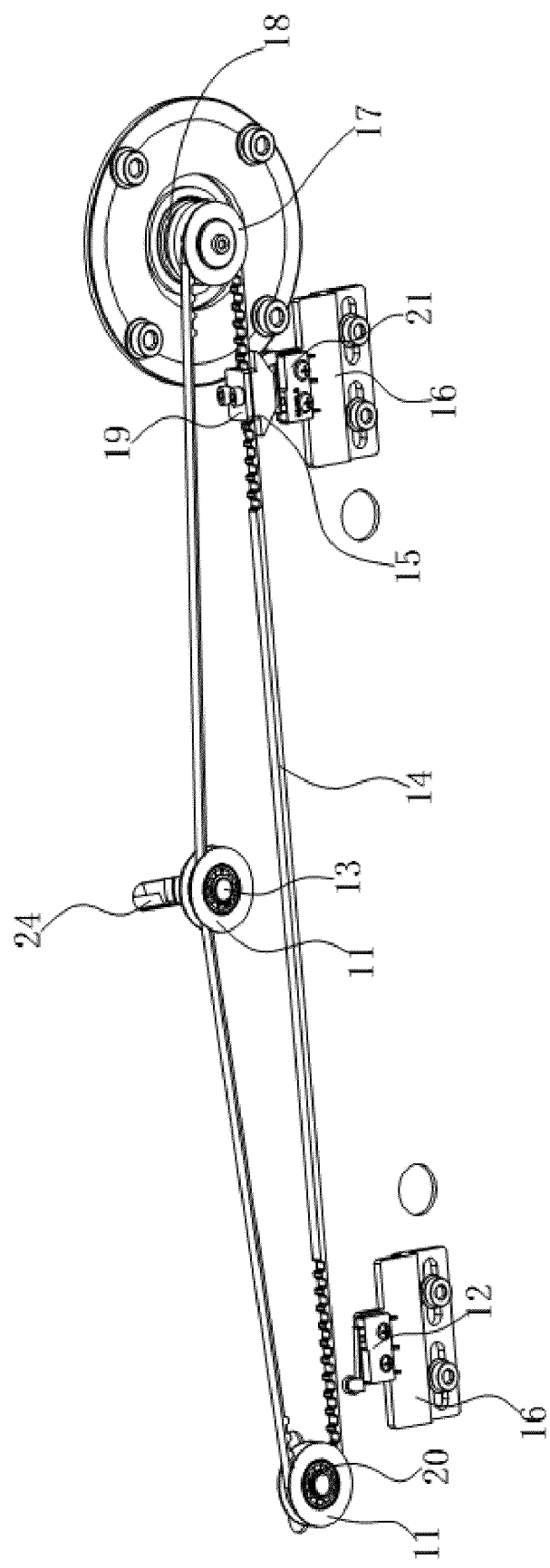
FIG. 3 is a perspective of mounting structures of a stroke control device.

As illustrated in FIGS. 1-3, one embodiment of a stroke control device includes a main body 7, a first driving mechanism 5, a second driving mechanism 1, a stopper 15, a first limit switch 12, and a second limit switch 21. The first driving mechanism 5 includes a rotating shaft 18, a drum 22, and a tether 23. The rotating shaft 18, which is disposed horizontally and arranged rotatably on the main body 7, is used to receive power output from a power supply device 4. The drum 22 is fixed coaxially with respect to the rotating shaft 18 on the middle thereof, such that the drum 22 rotates synchronously with the rotating shaft 18. The tether 23 is wound on the drum 22, such that one end portion thereof is connected with a carrier 2 and the other end portion thereof is connected with a balancer 3 being used for gravity balance against the carrier 2. One axial end of the rotating shaft 18 is in power-transmitting connection with the power supply device 4 fixed on the main body 7. The power supply 4 can be, for example, a motor. The first driving mechanism 5 drives the carrier 2 to move up-and-down vertically when the power supply device 4 operates.

In one embodiment, the second driving mechanism 1 includes a synchronous pulley 17, a synchronous belt 14, and a driven pulley 11. The synchronous pulley 17 is mounted coaxially with respect to the rotating shaft 18 on the other axial end thereof. There may be two driven pulleys 11, which present a triangular distribution together with the synchronous pulley 17. Each of the driven pulleys 11 is mounted rotatably on a supporting axle 13 through a bearing 20, and each of the supporting axles 13 is disposed horizontally and mounted on the main body 7, such that both of the two supporting axles 13 are parallel to the rotating shaft 18. The synchronous belt is tensioned on the synchronous pulley 17 and the two driven pulleys 11. Additionally, adjusting slots 24 are provided on the main body 7 at the positions corresponding to the two supporting axles 13, respectively, and end portions of the supporting axles 13 extend into the corresponding adjusting slots 24, such that the tension adjustment of the synchronous belt 14 is realized by moving the supporting axles 13 in the adjusting slots, allowing for proper tightness of the synchronous belt 14.

In the depicted embodiment, the stopper 15 is fixed on the synchronous belt 14 through a clamp 19. Driven by the synchronous belt 14, the stopper 15 reciprocates linearly in a horizontal direction. The first and second limit switches 12, 21 are both mounted on the main body 7 via a fixture 16, respectively, and the mounted position of each fixture 16 on the main body 7 is adjustable, enabling the adjustment of the linear spacing between the first and second limit switches 12, 21. By adjusting the linear spacing between the first limit switch 12 and the second limit switch 21, adjustment of the linear movement stroke of the stopper 15 is enabled, thereby achieving the limit control of the linear movement stroke of the carrier 2.

In one configuration, the power supply device 4 drives the carrier 2 to move vertically up-and-down through the first driving mechanism 5. The rotating shaft 18 drives the synchronous pulley 17 to rotate synchronously and convert the vertical up-and-down stroke of the carrier 2 into a linear movement stroke of the synchronous belt 14. The synchronous belt 14 drives the stopper 15 into a reciprocating linear movement, and the stopper 15 triggers the first and second limit switches 12, 21 during the movement, thereby achieving the limit control of the stroke of the carrier 2.

In the present embodiment, the synchronous pulley 17 acts as an input member for receiving power input from the first driving mechanism 5. The synchronous belt 14 acts as an output member for power output, the output member driving the stopper 15 into a linear movement. The linear movement stroke of the stopper 15 is less than the linear movement stroke of the carrier 2. By employing a synchronous belt transmission, the stopper fixed on the synchronous belt moves as the rotating shaft rotates. Such a configuration is simple in structure, light in weight, easy for installation, and effectively transmitting the movement angle of the rotating shaft without any desynchronizing. The linear spacing between the first and second limit switches and the linear movement stroke of the stopper can be obtained via calculation. Therefore, the structure is compact, the carrier stroke is easy to be adjusted, and the desired movement range can be ensured effectively. A proper tightness of the synchronous belt can be ensured by disposing two sets of driven pulleys.

The disclosed stroke control device includes a first driving mechanism driving a carrier into a linear movement, a first limit switch, a second limit switch, a stopper being able to trigger the first and second limit switches, and a second driving mechanism for driving the stopper into a linear movement. In one embodiment, the first driving mechanism includes a rotating shaft arranged rotatably on the main body for receiving power input, the second driving mechanism includes an input member rotating synchronously with the rotating shaft and an output member on which the stopper is fixed. The linear movement stroke of the stopper may be less than the linear movement stroke of the carrier.

In one embodiment, the first and second limit switches are provided on the main body and are spaced apart, and both switches are arranged on a path of the linear movement of the stopper. By triggering the first and second limit switches using the stopper moving linearly and by adjusting the linear spacing between the first and second limit switches, a mechanical control of the linear movement stroke of the carrier is realized, such that the entire stroke control device is simple in structure, easy for installation, convenient for adjusting the movement stroke range, and able to ensure a desired movement stroke effectively.

With regard to the second driving mechanism, the input member may be a sprocket, and the output member may be a chain. In one embodiment, the second driving mechanism further comprises a driven sprocket. The chain is tensioned on the sprocket, which is fixed on the rotating shaft, and the driven sprocket, which is arranged rotatably on the main body, the stopper being fixed on the chain. The input member may also be a gear fixed on the rotating shaft, and the output member may be a rack meshing with the gear, wherein the stopper is fixed on the rack, and the rack fits slidably in a linear guide rail which is fixed on the main body. The second driving mechanism may also be other structures which comprise an input member for receiving power from the first driving mechanism and an output member for outputting power, with the input member rotating with the rotating shaft synchronously, and the output member being fixed with the stopper such that the stopper can be moved linearly.

With regard to the first limit switch and the second limit switch, a mechanical triggering of the first and second limit switch can be achieved by the linear movement of the stopper.

The first driving mechanism may include a rotating shaft, a drum, and a tether. The rotating shaft and the drum may be an integral structure, or they may also be separate structures fixedly connected with each other. The first driving mechanism may also be other structures which are able to drive the carrier into a linear movement. The first driving mechanism has a rotating shaft for receiving power from a power supply device, which may be connected with the rotating shaft directly or may also be connected with the rotating shaft through a transmission mechanism. The power supply device acts as a power source and may be, for example, a motor.

The linear movement of the carrier may be a linear movement in a vertical direction, a linear movement in a horizontal direction, or a linear movement in a direction at an angle with respect to the vertical or horizontal direction. The linear movement of the stopper may be a linear movement in a vertical direction, a linear movement in a horizontal direction, or a linear movement in a direction at an angle with respect to the vertical or horizontal direction. Adjustment of the linear movement stroke of the carrier can be achieved by adjusting the linear spacing between the first limit switch and the second limit switch.

The stroke control device can be employed in a suspension type X-ray photograph system with the carrier being a telescopic cylinder which hangs an X-ray tube and the first driving mechanism driving the telescopic cylinder to move up and down in a vertical direction. The stroke control device may also be employed in other apparatuses or systems in which a limit control of a linear movement stroke is required.

Although the present disclosure has been described above in detail in combination with some particular preferred embodiments, those skilled in the art will recognize that the present disclosure not limited to these embodiments. It will understood by those skilled in the art that various modifications and changes may be made without departing from the disclosure and should be considered to fall into the scope of the disclosure.

The invention claimed is:

1. A stroke control device comprising:
   a first driving mechanism driving a carrier into a linear movement, the first driving mechanism comprising a rotating shaft arranged rotatably on a main body for receiving power input;
   a stopper being configured to move linearly;
   first and second limit switches defining a linear movement stroke of the stopper; and
   a second driving mechanism for driving the stopper into a linear movement, wherein the second driving mechanism includes an input member rotating synchronously with the rotating shaft and an output member on which the stopper is fixed, wherein the linear movement stroke of the stopper is less than the linear movement stroke of the carrier, and wherein the first and second limit switches are provided on the main body with a spacing therebetween and are both arranged on a path of the linear movement of the stopper.

2. The stroke control device according to claim 1, wherein the input member is a synchronous pulley and the output member is a synchronous belt, and wherein the second driving mechanism further comprises a driven pulley, wherein the synchronous belt is tensioned on the synchronous pulley and the driven pulley, the synchronous pulley is fixed on the rotating shaft, the driven pulley is arranged rotatably on the main body, and the stopper is fixed on the synchronous belt.

3. The stroke control device according to claim 2, wherein the driven pulley is arranged rotatably on a supporting axle through a bearing, wherein the supporting axle is arranged on the main body on which an adjusting slot is provided, and an end portion of the supporting axle extends into the adjusting slot.

4. The stroke control device according to claim 3, wherein there are two driven pulleys, wherein the two driven pulleys present together with the synchronous pulley a triangle distribution, and the rotating shaft and the supporting axles of the two driven pulleys are all disposed horizontally and parallel to each other.

5. The stroke control device according to claim 2, wherein the first and second limit switches are both arranged on the main body via a fixture of which the mounted position is adjustable.

6. The stroke control device according to claim 1, wherein the input member is a sprocket, the output member is a chain, and the second driving mechanism further comprises a driven sprocket, wherein the chain is tensioned on the sprocket and the driven sprocket, the sprocket is fixed on the rotating shaft, the driven sprocket is arranged rotatably on the main body, and the stopper is fixed on the chain.

7. The stroke control device according to claim 1, wherein the input member is a gear fixed on the rotating shaft, the output member is a rack meshing with the gear, the stopper is fixed on the rack, and the rack fits slidably in a linear guide rail fixed on the main body.

8. The stroke control device according to claim 1, wherein the first driving mechanism further comprises a drum fixed on the rotating shaft and a tether wound on the drum, wherein the carrier is connected with the tether, and wherein the diameter of the drum is larger than the diameter of the input member.

9. The stroke control device according to claim 8, wherein the tether is further connected with a balancer for gravity balance of the carrier.

10. The stroke control device according to claim 9, wherein the carrier is a telescopic cylinder with an X-ray tube hung thereon in an X-ray photograph system, and wherein the telescopic cylinder is connected with the tether and moves up and down in a vertical direction.

* * * * *